United States Patent [19]

Mody et al.

[11] 4,245,509
[45] Jan. 20, 1981

[54] SAMPLING APPARATUS

[75] Inventors: Dinesh I. Mody, Bedford, Mass.; Carolyn Bergkvist, Plaistow, N.H.; Gustav H. Dreier, Acton, Mass.

[73] Assignee: Instrumentation Laboratory Inc., Lexington, Mass.

[21] Appl. No.: 21,069

[22] Filed: Mar. 16, 1979

[51] Int. Cl.$^3$ .............................................. G01N 1/14
[52] U.S. Cl. .................................................. 73/423 A
[58] Field of Search ...................... 73/422 GC, 423 A; 422/64, 65, 68

[56] References Cited

U.S. PATENT DOCUMENTS

| | | | |
|---|---|---|---|
| 3,419,358 | 12/1968 | Smythe et al. | 73/423 A |
| 3,609,040 | 9/1971 | Kuzel | 73/423 A |
| 3,858,450 | 1/1975 | Jones | 73/423 A |
| 3,884,802 | 5/1975 | Spaans | 73/422 GC |
| 3,900,289 | 8/1975 | Liston | 73/423 A |
| 3,940,995 | 3/1976 | Harris et al. | 73/422 GC |

*Primary Examiner*—S. Clement Swisher

[57] ABSTRACT

Sampling apparatus designed for aspirating, diluting and mixing a small sample of fluid in precise amounts and delivering the mixture to a scientific apparatus at a place remote from the place of aspiration. Operation of the device may be manual but is preferably automatic. The apparatus is designed to process a plurality of sample fluids with no cross-contamination between samples. In essence, the apparatus is a fluid handling system including a sample pick-up assembly in fluid communication with an automatic valve assembly having two operative positions. The automatic valve assembly is in fluid communication with a dilutor assembly having a sample pump and a diluent pump operable by a common means. A mixing and delivery assembly is also in fluid communication with the automatic valve assembly and includes a cup designed for bidirectional rotation with an annular space about the cup. A dispensing probe dispenses into the cup precise amounts of sample and diluent in a predetermined ratio to each other and, following rotation of the cup to achieve the mixture of sample and diluent, an aspirator probe enters the mixture and delivers an amount thereof to an adjacent scientific instrument. The apparatus further includes a means for expelling the remainder of the mixture from the cup into the annular space surrounding the cup, and from there through a valve, to waste.

20 Claims, 11 Drawing Figures

SAMPLING APPARATUS

BACKGROUND OF THE INVENTION

1. Field of the Invention

The present invention relates to a sampling apparatus designed precisely to aspirate, dilute and mix a small sample of fluid, such as a biological fluid which may be whole blood, serum, plasma, spinal fluid, etc., with a suitable diluent and deliver the resultant mixture to a scientific instrument for appropriate measurement or analysis thereby. The apparatus may be operated either in manual or automatic mode and is designed with capability to deliver the mixture at a place remote from the sample aspiration. The apparatus, furthermore, is designed to process a plurality of samples with no cross-contamination between the samples.

2. Description of the Prior Art

Admittedly, some parts of the sampling apparatus of the invention have been disclosed in the prior art, but nowhere has the combination of such an apparatus, nor some other parts, have even been hinted at, especially with the features and advantages as hereinbelow more fully described.

For instance, U.S. Pat. No. 3,900,289 that issued to Max D. Liston on Aug. 19, 1975, entitled "Apparatus and Method for Filling a Compartment," discloses basically a specimen dispenser designed to fill a compartment to a predetermined level with an aqueous solution taken from a reservoir. The dispenser includes a hollow probe nozzle designed to withdraw solution from the reservoir and is then moved to the vicinity of the compartment in order to deposit a predetermined amount of the solution into the compartment. It specifically discloses a carousel-type arrangement in which both the reservoir and the compartment are concentrically mounted in the carousel.

A further U.S. Pat. No. 3,858,450 that issued to Alan R. Jones on Jan. 7, 1975, entitled "Sample Mixing and Metering Apparatus," discloses a sampling head including a hollow pick-up probe for extracting a given amount of sample from a sample cup. The probe is movable between a sampling position and a retracted position. A valve mechanism connected to the probe is of the face-valve type in which two blocks are linearly slideable relative to one another between two valve positions, a sampling position and a delivery position. An air cylinder moves not only the probe but also operates this sliding valve. In the delivery position, the face-valve effects fluid connections for mixing a given amount of sample with another fluid and for delivering the mixture to a receptacle.

A further patent, U.S. Pat. No. 3,940,995, granted Mar. 2, 1976, to R. J. Harris Sr. et al., entitled "Automatic Fluid Injector," discloses an injector designed for accurately measuring and injecting quantities of fluid specimens into various media which may be a receptacle or an inlet of a scientific instrument. The injector essentially comprises three sub-assemblies including a syringe assembly, an injector feed assembly and a feed tray for transporting specimen-containing vials to the injector feed assembly. A reciprocable hollow probe associated with the injector feed assembly is designed to pick up a fluid specimen and convey the same to the syringe of the syringe assembly. Automatic contols are also disclosed for cyclically cleaning, purging, filling and injecting fluid specimens into an analytical instrument.

SUMMARY

The principal object of the present invention is to provide an automatic sampling apparatus designed for precisely aspirating, diluting and mixing a small amount of sample fluid with a diluent and delivering the mixture thereof to a scientific instrument at a place remote from the place of aspiration of the sample. The apparatus is further designed to take into its dilutor assembly a predetermined amount of sample and a predetermined amount of diluent in a predetermined ratio one to the other so that both sample and diluent may be conveyed to a mixing and delivery assembly in a precise ratio one to the other. The delivered sample and diluent in the mixing and delivery assembly is then rapidly mixed, following which a portion thereof is ready for delivery to a scientific instrument to be measured or analyzed thereby. The apparatus of the invention also includes a means for expelling the remainder of the mixture to waste so as to avoid cross-contamination between successive samples.

Although any suitable scientific instrument may be used with the apparatus of the invention, the preferred instrument shown herein is a flame photometer designed to provide rapid and accurate determinations of parameters, such as sodium, potassium, lithium, and if desired, cesium, in a mixture of serum or urine and a suitable diluent. In this preferred scientific instrument, the internal standard and the particular preferred diluent are both the same, namely cesium. This permits effortless analyzation of the same sample, at least as far as the sodium, potassium and lithium values are concerned.

Essentially, the sampling apparatus of the invention comprises a sample pick-up assembly designed to cooperate with a suitable means automatically positioning seriatim a plurality of sample cups containing sample fluids in the vicinity of the sample pick-up probe of this assembly. This sample pick-up assembly is in fluid communication with an automatic probe assembly that includes an automatic probe operable in one of two operative positions and mounted within a suitable housing provided with at least two channels therein. The automatic probe is formed with a side port communicating with its internal longitudinal channel and is also provided with a through-port adjacent and spaced from the side port in the solid end thereof. In one of the operative positions of the automatic probe within the housing, its side port is in communication with one of the channels in the probe housing and in its second operative position, the probe's side port is in communication with the other channel found in the probe housing. Preferably, there is also a further channel formed in the probe housing which is designed to provide venting to the atmosphere when aspirating high viscosity samples, such as whole blood. The through-port of the probe is designed to align itself with one or the other through-channels in the housing, it being noted that one of the channels is only a half-channel communicating only with the vertical channel formed in the housing to accommodate the probe therein.

An object of the present invention is to have such a sampling apparatus that can precisely aspirate, dilute, mix and deliver small samples one after another to a scientific instrument at a place remote from the place of aspiration in which the ratio of the sample to the diluent has been precisely set. It is a further object of the invention to provide such an instrument which can process a plurality of samples rapidly and automatically, yet with no cross-contamination between successive samples. It is also an object of the present invention to provide a sampling apparatus which can effectively purge itself inbetween delivering different mixtures of sample and diluent to a scientific instrument. It is a still further object of the present invention to provide a sampling apparatus that can evacuate the remainder of the mixture after the delivery of a portion thereof into the scientific instrument. It is yet another object of the present invention to provide an apparatus that can work with very small fluid samples (on the order of about 225 $\mu l$ to about 275 $\mu l$) in a relatively simple, inexpensive manner, and that can be serviced easily by having handily available parts, most of which are designed for easy replacement.

The characteristics of preferred sampling apparatus constructed in accordance with the present invention will be more fully understood by reference to the following detailed description of preferred embodiment and to the accompanying drawings to which reference is made in the detailed description. Similar reference characters are used to represent similar parts or components in the different figures.

BRIEF DESCRIPTION OF THE DRAWINGS

These and other advantages and features of the present invention will hereinafter appear for purposes of illustration, but not of limitation, in connection with the accompanying drawings in which.

DESCRIPTION OF THE PREFERRED EMBODIMENT

Figure 1:
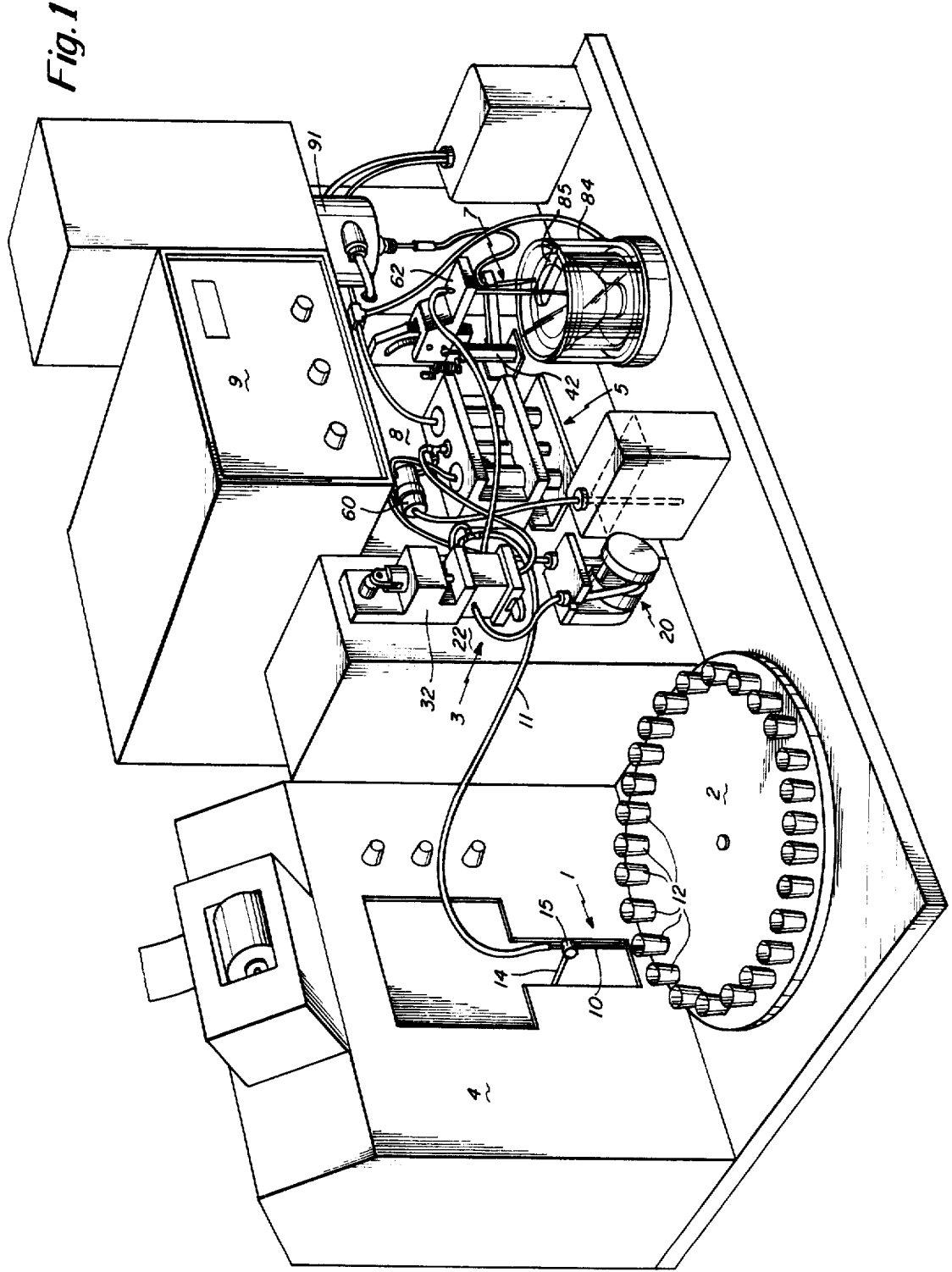
FIG. 1 is a perspective view of a preferred form of sampling apparatus constructed in accordance with and embodying the present invention in which the several sub-assemblies of the overall combination are designated by single digit numerals.
Figure 2:
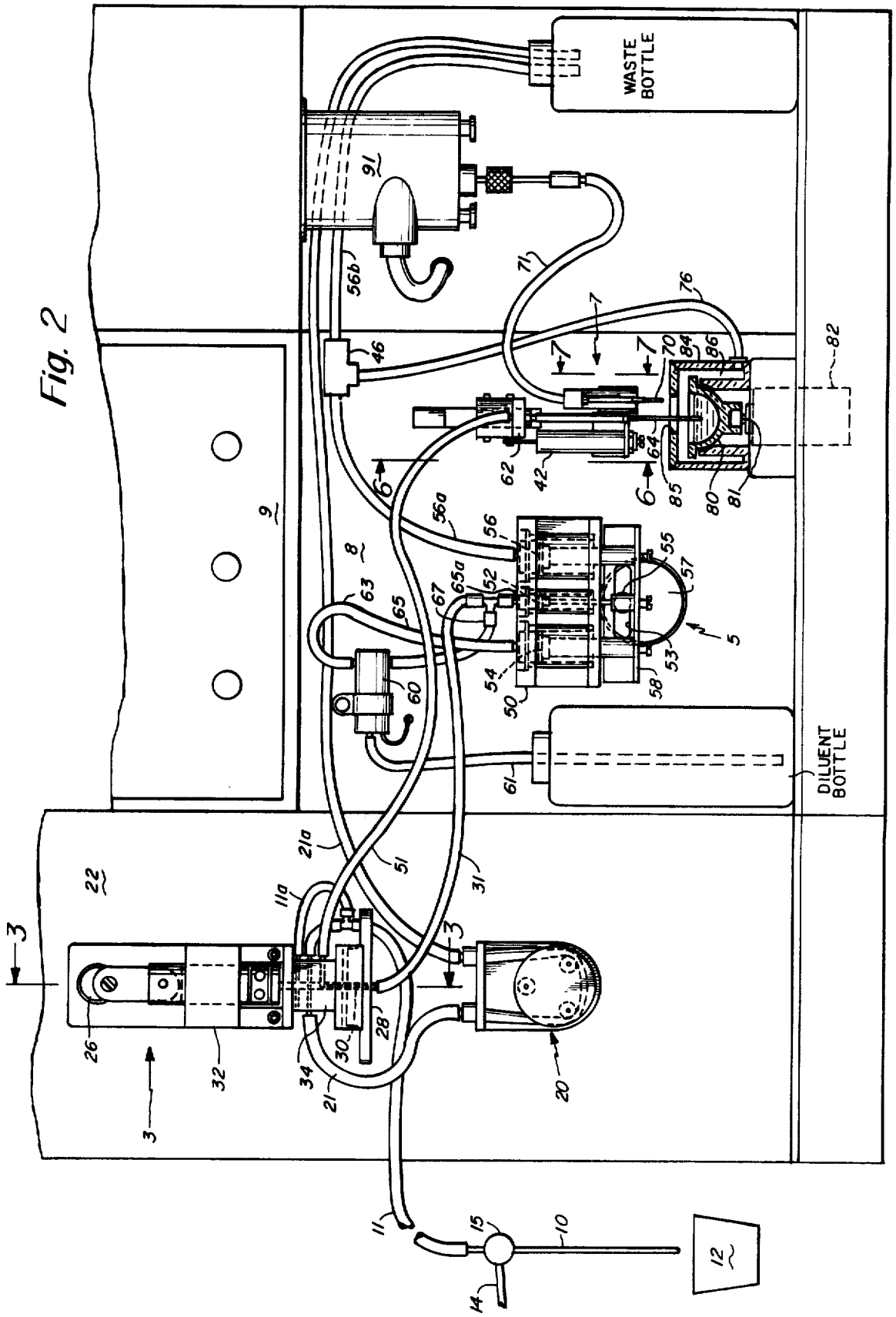
FIG. 2 is a front elevational view of portions of the preferred form of sampling apparatus shown in FIG. 1 but on an enlarged scale and with parts of the background instruments broken away for clarity.

Referring to the drawings and in particular to FIGS. 1 and 2, the preferred form of a sampling apparatus made in accordance with and embodying the present invention is shown therein, first in perspective and second in front elevation, together with a preferred form of a scientific instrument with which it may be associated, such as a flame photometer.

The several sub-assemblies of the overall combination of the sampling apparatus of the invention are designated thereby by single digit numerals. One of such sub-assemblies is the sample pick-up assembly 1 which is shown mounted adjacent a suitable sample tray 2 containing a plurality of sample cups 12 which have been previously filled with sample fluids, all as is well known in the art. This sample tray 2 is designed to present these sample cups 12, one after the other, to the vicinity of a sample pick-up probe 10 which may be releasably secured as at 15 to an arm 14 of an instrument 4 designed to lower arm 14 and thereby pick-up probe into a just indexed sample cup 12. Following the sample pick-up from this cup, the instrument 4 effects first, the raising of arm 14 and thereby pick-up probe 10 from the sample cup 12, and second the indexing of sample tray 2 so as to present another sample cup 12 into the vicinity of pick-up probe 10, at which point instrument 4 once again effects the lowering of arm 14 and thereby pick-up probe 10 into the newly presented sample cup 12, all as is well known in the art. The upper free end of the sample pick-up probe 10 is connected to a flexible pick-up tube 11 which communicates with one of the channels formed in the housing of the automatic probe assembly 3, all as will be more fully described below. The other end of the particular channel of the probe assembly 3 is connected by flexible tube 21 to a peristaltic pump assembly 20 and from hence, via a further flexible tube 21a, to a suitable waste bottle.

Figure 4:
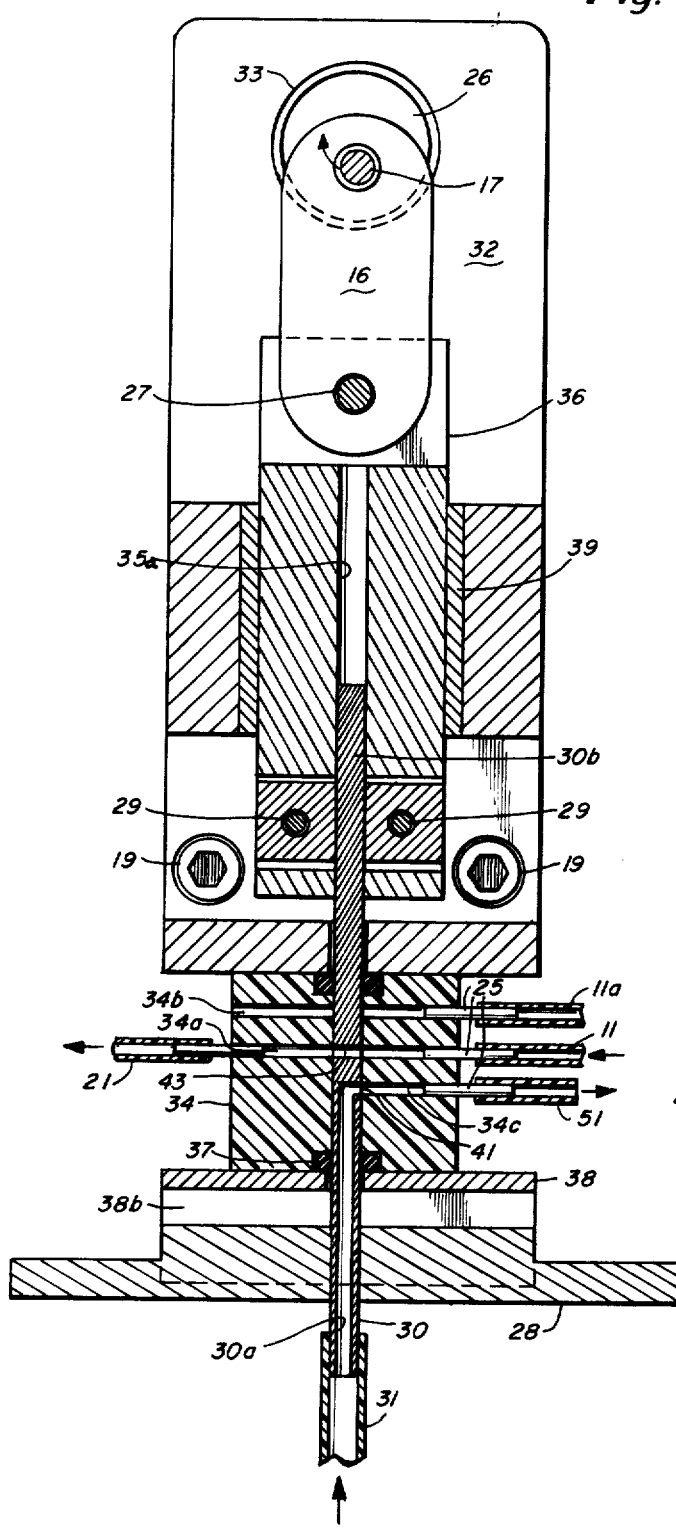
FIG. 4 is a vertical front section, partly in elevation, of the automatic probe assembly shown in FIG. 3 and taken along the line 4—4 thereof.
Figure 5:
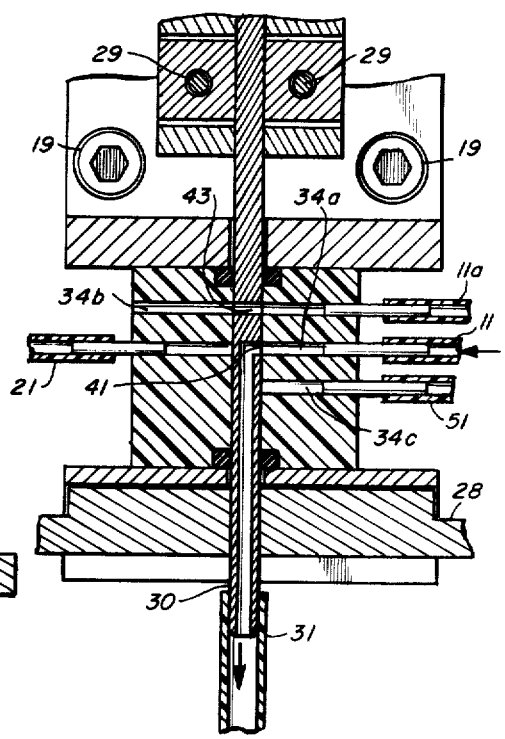
FIG. 5 is a view similar to FIG. 4 but with portions broken away and showing the automatic probe of the probe assembly in a different operative position from that shown in FIG. 4.

The automatic probe 30 of the probe assembly 3 is mounted within its housing 32 in a vertical longitudinal channel thereof and its operation will be more fully described below with further reference to FIGS. 3, 4 and 5. The bottom end of the automatic probe 30 is connected by flexible tube 31 to the dilutor assembly 5 whose operation will also be more fully described below. The dilutor assembly 5 is furthermore in fluid communication via suitable flexible tubes 63 and 61 with the aid of a solenoid-operated three-way valve 60, to a diluent bottle containing the required diluent (herein cesium) for the particular scientific instrument with which the sample apparatus is preferably employed, here being displayed as a flame photometer 9. The third exit of this 3-way valve 60 finds connection to flexible tube 65 and thereby via a T connection 67, is connected to flexible tube 31 which, as already mentioned, furnishes fluid communication between the automatic probe assembly 3 and the dilutor assembly 5 of the sampling apparatus of the invention.

Essentially, the dilutor assembly comprises a sample pump 52 and a dilutor pump 54 mounted within housing 50 in a manner in which both pumps are operable by a common means which may be a common drive plate 58. Although not forming part of the dilutor assembly 5 per se, there is shown a further piston-cylinder pump 56 mounted in the dilutor housing 50 and also operable by the same common means, namely the common drive plate 58. This is a pump that is designed to withdraw the remainder of the mixture of sample and diluent from the mixing and delivery assembly 7 and, following withdrawal through a check valve 46 and flexible tube 56a, it expels the same into a waste bottle via flexible tube 56b when the common drive plate 58 is operated, as more fully described below. Waste pump 56 is mounted in the dilutor housing 50 for purposes of simplicity of construction and ease of operation.

A further sub-assembly is represented by the numeral 7 and it designates the mixing and delivery assembly of the sampling apparatus of the invention. As may be noted, this mixing and delivery assembly 7 is, on the one hand, in fluid communication via flexible tube 51 with a further channel formed in the housing of the automatic probe assembly 3 and via flexible tube 71, with the particular scientific instrument 9, herein a flame photometer, and more particularly, the atomizer assembly 91 of such a flame photometer.

As already mentioned, the preferred embodiment of the sampling apparatus of the invention has been designed to aspirate, dilute, mix and deliver a mixture of a sample fluid in precise ratio to a suitable diluent, herein cesium, and at a place remote from the place of sample pick-up, and yet do this relatively simply and with no cross-contamination between successive samples and also at a sufficiently fast pace to mesh with the cycle time of the particular scientific instrument.

A further significant segment of the mixing and delivery assembly 7 is represented by a spinning cup 80 that is mounted for fast and bi-directional rotation within a suitable housing 84 provided with an opening 85 at its top. The cup 80 is rotatably and preferably releasably mounted on a shaft 81 of a suitable electric motor 82 mounted below and preferably concentrical with the housing 84. As may be further noted, the side of the housing 84 is formed with two concentric walls defining an annular space 86 about and surrounding the lip of the spinning cup 80. This annular space 86 is essentially enclosed save for the top opening 85 which is provided to allow the entry therethrough and into the cup 80 of first the dispensing probe 64 to dispense therein a predetermined and measured quantity of sample and diluent and, following the mixing thereof by the rotation of the cup 80, to withdraw a portion of the resultant mixture therefrom through the aspirator probe 70, all as more fully described below.

The detailed construction of the automatic probe assembly 3 will now be described with particular reference to FIGS. 3, 4 and 5. It includes an automatic probe 30 designed for vertical displacement within a suitable longitudinal vertical channel 35 formed within the probe housing 32. The automatic probe 30 is essentially a hollow tube formed with a longitudinal inner channel 30a and provided with a side port 41. The upper or forward end 30b of the probe is solid except for a through-port 43 which is formed adjacent and parallel with the side port 41 and somewhat spaced therefrom. This through-port 43 extends diametrically across the probe 30.

Figure 3:
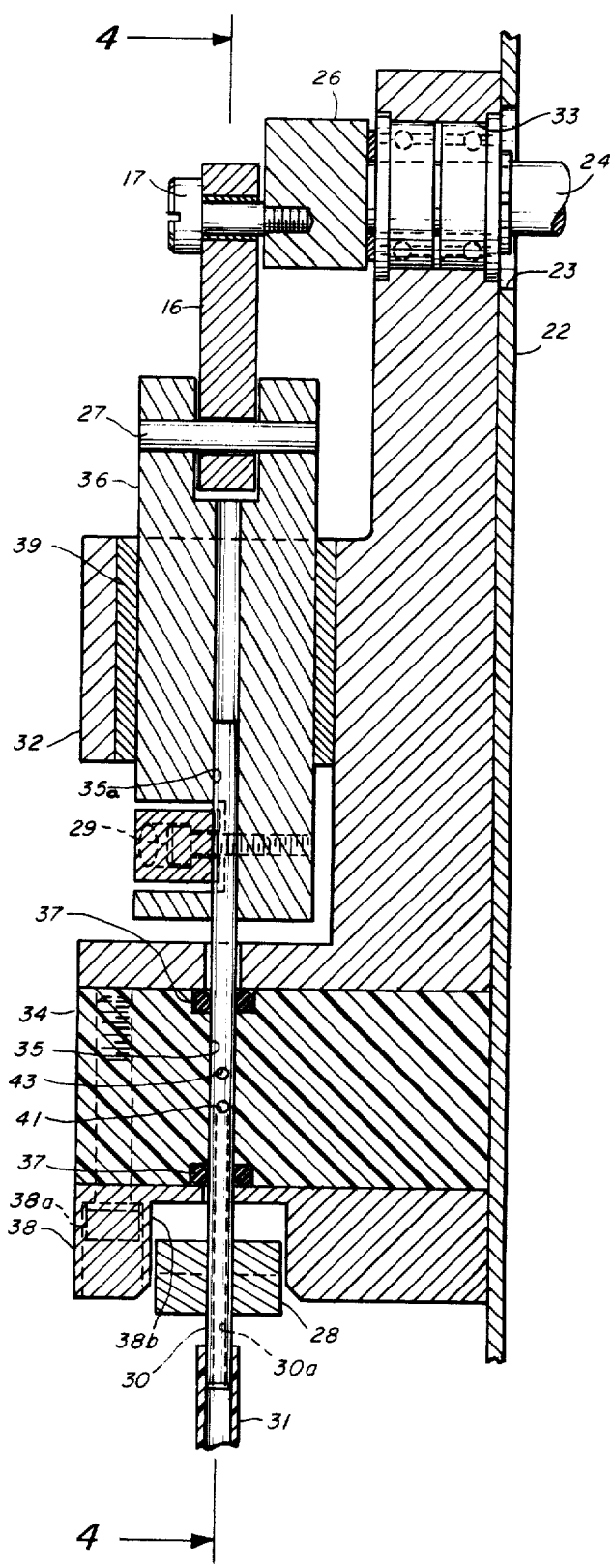
FIG. 3 is a vertical side section taken along the line 3—3 of FIG. 2 but on a still larger scale and showing the detailed construction of the automatic probe assembly of the sampling apparatus.

As may be best observed in FIG. 3, the automatic probe assembly may be conveniently attached to a front vertical plate 22 of a housing, which may be specifically designed to support it alone or which may form part of an instrument. The assembly may be secured thereto by any convenient means such as a pair of bolts 19, note FIG. 4. The vertical plate 22 is provided with an opening 23 to accommodate a shaft 24 therethrough, which may be driven by any known means, such as an electric motor (not shown). Adjacent opening 23, there is a further abutting opening 33 provided in the housing 32 to accommodate suitable bearings for the shaft 24 and a member 26 protruding therefrom and mounted for rotational displacement by the shaft 24. An eccentrically mounted bolt 17 connects member 26 to a suitable link member 16 whose other end is connected by pin 27 to a prove moving member 36 slidably mounted within bushing 39 disposed in the housing 32. The solid end 30b of the probe 30 is secured within the vertical channel 35a of member 36 by means of a pair of set screws 29 so that it may be displaced in translation within channel 35 when member 36 is vertically displaced by link 16.

As may be further observed, the upper portion of the probe housing 32 may be formed of metal, say stainless steel, but its fluid handling portion preferably is comprised of a removable plastic block 34, such as Teflon. There are at least two horizontal channels formed in block 34 in a direction normal to the axis of the vertical channel 35 also formed in block 34 to accommodate probe 30 therein. One such channel 34a is a through channel that passes through block 34 transversely and is provided with suitable fittings 25 equidistantly positioned both within and without the channel so as to accommodate removably on the free ends thereof flexible tube 11 on one side and flexible tube 21 on the other. Somewhat spaced below through-channel 34a is a half-channel 34c that is parallel therewith and communicates radially with vertical channel 35. The distance separating side port 41 from through-port 43 in probe 30 is identical with the distance separating half-channel 34c from through-channel 34a. The diameters of these channels 34a and 34c are preferably somewhat smaller than the diameters of side port 41 and through-port 43 of the probe 30.

There is preferably provided in block 34 another through-channel 34b that runs parallel with channel 34a and is positioned equidistantly therefrom same as channel 34c. This through-channel 34b is provided with only one side fitting 25 to accommodate a flexible tube 11a communicating with tube 11 through a T connection, not shown. Channel 34b serves as a convenient vent hole to atmosphere when aspirating high viscosity samples, such as whole blood and the like.

Since the operative connection between fluid moving through the tubes and into automatic probe 30 is effected within this plastic block 34, its vertical channel 35 is preferably sealed with respect to the vertically displaceable probe 30 therethrough by means of a pair of "O" rings 37. A bottom plate 38, which may be formed of the same metallic material as housing 32, is provided removably to secure the plastic block 34 in place through bolts 38a. Preferably, the bottom plate 38 is formed with a channel 38b designed to accommodate a guide member 28 fitted about the lower end of probe 30 so as to facilitate its travel within the housing. FIGS. 3 and 4 show the automatic probe 30 in its "down" operative position in which its side port 41 is aligned with the half-channel 34c and the through-port 43 is aligned with the through-channel 34a. In contrast, FIG. 5 shows the automatic probe 30 in its second "up" operative position in which its side port 41 is aligned with through-channel 34a and its through-port 43 with through-channel 34b. It should be noted that in this operative position, the half-channel 34c is effectively blocked by the probe 30.

As may be noted in FIG. 2, in particular the dilutor assembly 5 thereof, an eccentrically mounted roller 55 on rotatable member 57 is designed to ride within and cooperate with slot 53 formed in the common drive plate 58. By the rotational displacement of roller 55, rotational motion is converted to a motion in translation to common drive plate 58 which in turn drives the respective pistons of the several pumps within their respective cylinders.

This is, of course, similar to effecting the translational motion to the automatic probe 30 within its housing 32 by the combination of an eccentrically mounted bolt 17 on rotatable member 26. As has already been mentioned, the common drive plate 58 also effects the working of the waste pump 56, which for convenience is mounted adjacent pump 52 and 54 and in the same housing 50 of the dilutor assembly 5.

Figure 6:
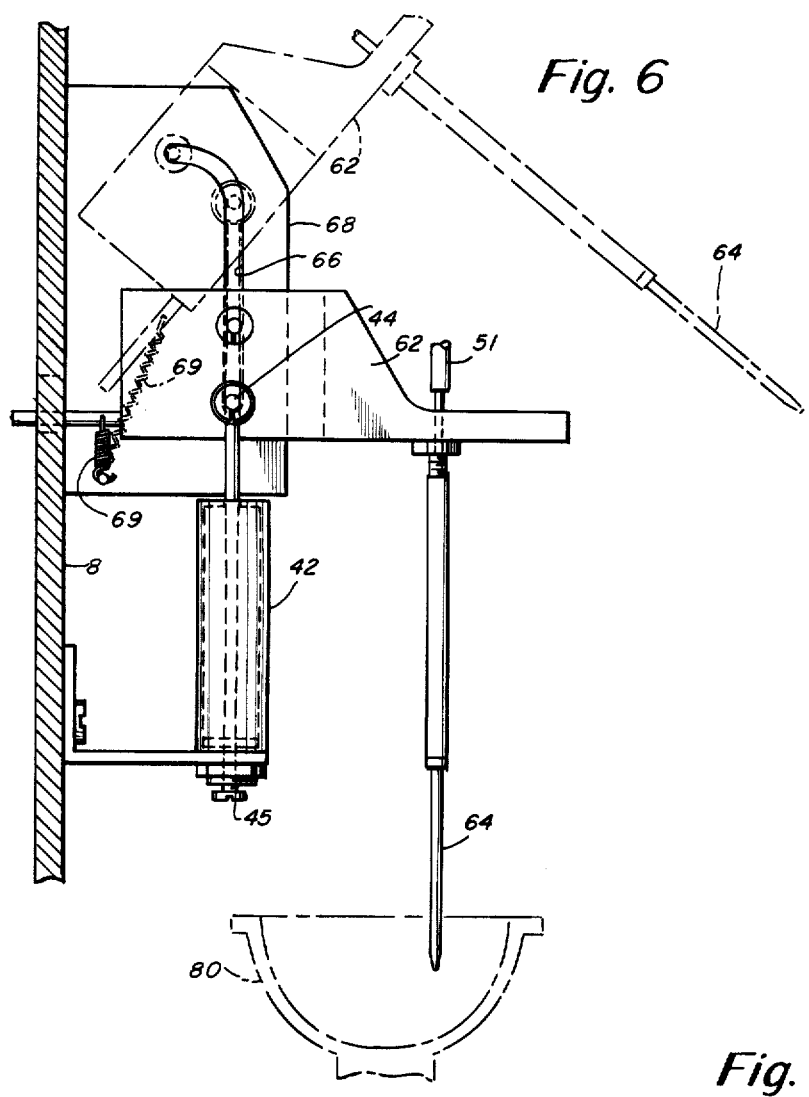
FIG. 6 is a side elevation of a part of the mixing and delivery assembly of the sampling apparatus taken along the line 6—6 of FIG. 2 and showing the dispensing probe in its two operative positions with respect to a spinning cup, with the normally down position in solid lines, and the upward position in phantom lines, the latter position being employed for manual operation only.

FIG. 6 is a side elevation of a part of the mixing and delivery assembly 7 and shows the dispensing probe 64 in its two operative positions with respect to the spinning cup 80 already described. The normal "downward" position is shown in solid lines and its "up" position in phantom lines, it being noted that the "up" position is used only for manual operation. Dispensing probe 64 is releasably mounted on arm 62 which is spring biased by tension spring 69 in its normal downward position. Arm 62 is mounted on the front lower plate 8 of the scientific instrument by means of a support and guide member 68 provided with a channel 66. Arm 62 is provided with a pin 44 designed to ride within this channel 66. When operator is moving arm 62 upward to assume the position shown in phantom lines, pin 44 and channel 66 cooperate, first to effect a vertical motion to the dispensing probe 64 and thereafter an arcuate motion, until tube 64 assumes the position as shown against the tension of spring 69, now fully extended. When desired to return the dispensing probe 64 to its normal downward position, the operator moves arm 62 downward. In order to cusion the force exerted by tension spring 69 to accelerate the downward motion of the probe 64, pin 44 also is operatively connected to a dash pot 42 of known design and construction also mounted on the front plate 8 of the scientific instrument. A convenient dash pot adjustment 45 in the form of a set screw may be provided to adjust the extent of its lowermost travel, and thereby, the extent of travel of probe 64 as is well-known to those skilled in the art.

Figure 7:
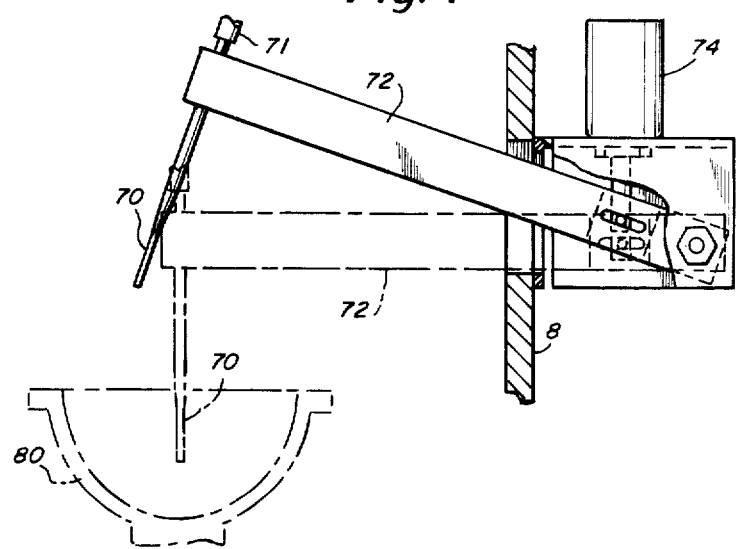
FIG. 7 is a vertical elevation of another part of the mixing and delivery assembly and taken along the line 7—7 of FIG. 2, showing especially the aspirator probe in its two operative positions, namely the normally up position shown in solid line and the lower position in phantom line when the same is to aspirate the mixture of sample and diluent from the spinning cup.

In FIG. 7 is shown in vertical elevation another part of the mixing and delivery assembly 7, namely the aspirator probe 70 also shown in its two operative positions, namely in its normally "up" position shown in solid lines and its "down" position shown in phantom lines when the aspirator probe 70 is designed to enter into the mixture of sample and diluent contained in spinning cup 80 so as to aspirate a portion thereof and transmit the aspirated mixture via flexible hose 71 to the atomizer assembly 91 of a scientific instrument 9, herein shown to be a flame photometer. The force for aspirating the mixture via probe 70 may be effected, as it is herein, by a pump means of the scientific instrument 9 itself or, of course, the sampling apparatus of the invention may be provided with a further pump means to effect such aspiration when the same is used in conjunction with scientific instruments which do not possess such a built-in pump means.

In a fashion similar to the dispensing probe 64, aspirator probe 70 is also releasably secured to an arm 72 which is, however, moved here by means of a solenoid-operated member 74 operatively connected to arm 72 and operated in a manner all as is well-known to those skilled in the art. Also, as may be noted in FIG. 7, the solenoid-controlled arm 72 is attached to the back of the front plate 8 of the scientific instrument 9.

The operation of the sampling apparatus of the invention will now be described with reference to FIGS. 8, 9, 10 and 11 which are schematics and depict the various operative positions of the sampling apparatus.

Figure 8:
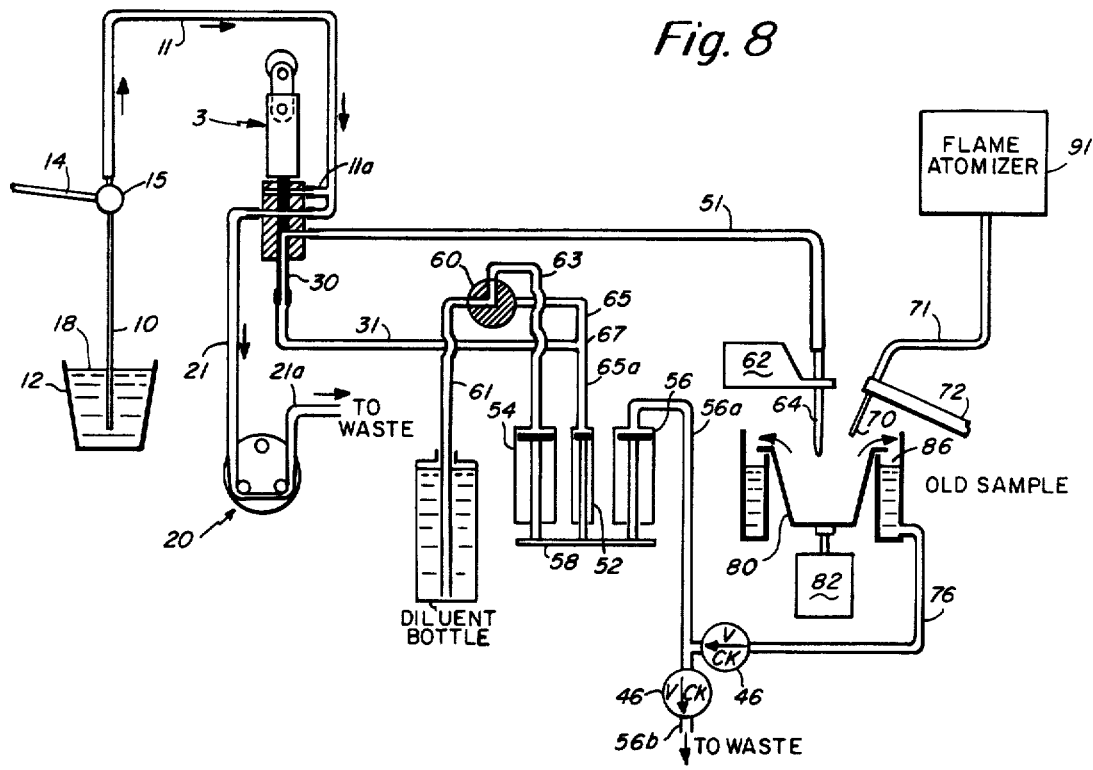
FIGS. 8, 9, 10 and 11 are schematic views of the sampling apparatus of the invention and depict its various operative positions which will be referred to when explaining its operation.

FIG. 8 depicts an operative position where sample pick-up probe 10 is lowered into sample cup 12 containing a particular fluid sample 18, which preferably is a biological fluid such as whole blood, serum, plasma, spinal fluid, or the like. The automatic probe assembly 3, in particular its automatic probe 30 thereof, is in its "down" operative position as shown and described with reference to FIGS. 3 and 4 and in which flexible tube 11 connects via through-port 43 and tube 21 with the peristaltic pump assembly 20 and hence via tube 21a to waste. Consequently, any sample 18 aspirated at this time fills tubes 11 and 21 and 21a and in effect purges the same from the traces of the previous sample. It should be noted that purging of the tubes may also be enhanced by aspirating air through pick-up tube 10 before the same is immersed into fluid sample 18.

Aspirator probe 70 is in its normal "up" position, i.e., removed from the spinning cup 80, from which the remainder of the previous mixture of sample and diluent has just been expelled through the rotation of the spinning cup at very high speeds, about 6000 rpm, into the annular space 86 surrounding the cup 80. One should also observe the position of the solenoid-operated 3-way valve 60, together with the position of the common drive plate 58 which has been moved all the way to its uppermost position, displacing thereby the respective pistons of the sample and diluent pumps, and also of the waste pump in an upward position. The 3-way valve 60 now connects the diluent pump 54 via flexible tubes 63 and 61 with a supply of diluent contained in a diluent bottle, which diluent is herein preferably cesium. The sample pump 52 is connected via flexible tubes 65a and 31, which are joined by a T connection with further flexible tube 65, to the automatic probe 30. The side port 41 of probe 30 now effectively communicates with half-channel 34c and hence through flexible tube 51 to the dispensing probe 64.

Figure 9:
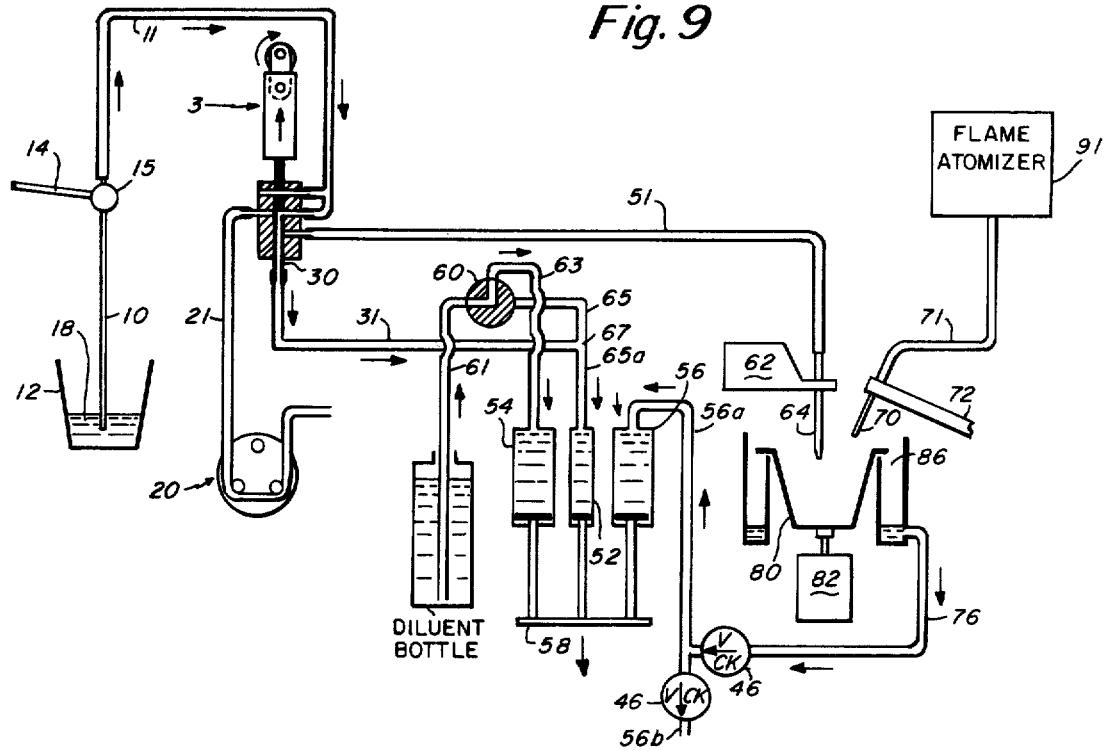

The next operative position of the sampling apparatus of the invention is depicted in FIG. 9. First, the automatic probe 30 is moved to its second "up" operative position as shown in and previously described with reference to FIG. 5, by rotational displacement of the eccentrically mounted bolt 17 on member 26, so as to align side port 41 with one half of the through channel 34a, and concomitantly therewith, to align through-port 43 with through-channel 34b. Thereupon, the common drive plate 58 of the dilutor assembly 5 is moved downward by the eccentrically mounted roller 55 bearing against the slot 53 of plate 58. Roller 55 is rotationally displaced by the rotatable member 57 to which it is attached. As a consequence, the respective pistons of the piston-cylinder pumps 52, 54 and 56 commence their downward motion with the following respective results: sample pump 52 draws in a predetermined amount of sample through probe 30 and tube 31 into its cylinder, while diluent pump 54 draws in diluent through tubes 63 and 61 which are effectively connected by 3-way valve 60 as shown. At the same time, waste pump 56 effects the removal of the expelled sample/diluent mixture from the annular space 86 via tube 76 and hence through check valve 46 and tube 56a. It should be noted that check valve 46 essentially accomplishes two functions and is consequently represented in these figures as comprising two. One of its functions is to prevent any mixture from returning into tube 76 once it has passed therethrough. Its second function is to permit mixture to pass through tube 56b to waste during the next operative step as will be described with reference to FIG. 10. Thus, by this operation, the dilutor assembly 5 of the sampling apparatus has been filled with a predetermined amount of sample and a predetermined amount of diluent in which the ratio of sample and diluent has been predetermined by the respective diameters of pumps 52 and 54 and their relation to each other.

Following the operative step just described with reference to FIG. 9 in which a measured predetermined quantity of sample and diluent have been introduced into the dilutor assembly 5 by the downward displacement of the common drive plate 58, we come to the next operative position that will now be described with reference to FIG. 10. It should be noted first that the position of the automatic probe 30 will once again be in its "down" position as shown in FIG. 4, connecting its side port 41 with half channel 34c and thus to flexible tube 51 and dispensing probe 64 thereby. After the automatic probe 30 assumes this "down" position, the common drive plate 58 will commence its upward motion through the rotational displacement of the eccentrically mounted roller 55 on rotatable member 57, and transmitting the same via channel 53 to plate 58, all as previously described.

It should be especially noted that the position of 3-way valve 60 has also been changed so that the same now connects the diluent pump 54 via its flexible tube 63 to flexible tube 65, and hence through T connection 67 to tube 31 which, as already mentioned, is also connected by the same T connection 67 to tube 65a and thereby to sample pump 52. As a consequence, when common drive plate 58 drives the respective pistons of pumps 52 and 54 upward, the respective measured amounts of fluid sample and diluent contained in the respective cylinders thereof are driven from these through the tubes substantially in the direction of the arrows shown. It should also be noted that when the volume of the fluid sample aspirated during the operative step described with reference to FIG. 9 is very small, say of the order of between 16 μl to 32 μl, the aspirated sample then is essentially contained in the automatic probe 30 and perhaps a portion of tube 31 only, with the remainder of the tubes primed with diluent. This is particularly so where the ratio of sample to diluent is, as preferred, 1 to 100.

Figure 10:
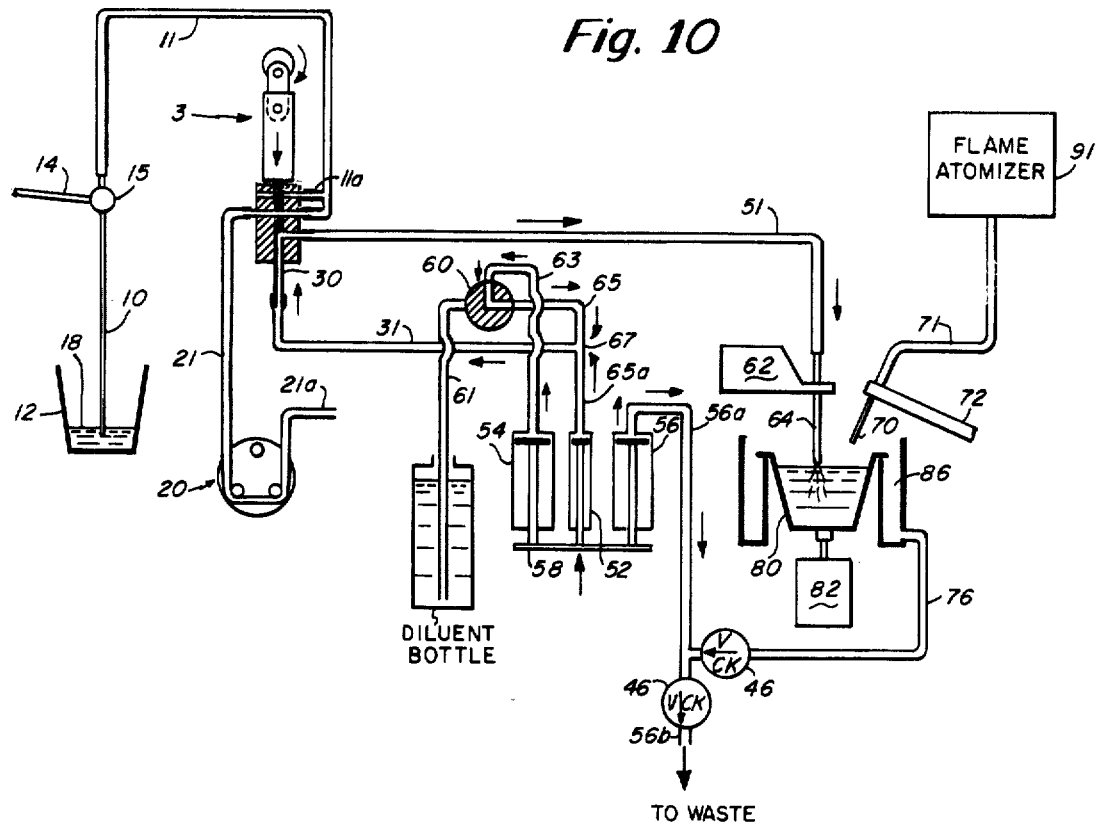

When the respective pistons of pumps 52 and 54 have reached their uppermost travel as shown in FIG. 10, the respective predetermined amounts of sample and diluent will have been duly dispensed by dispensing probe 64 into spinning cup 80. The aspirator probe 70 is still in its "up" position.

A further function is also effected by the common drive plate 58 and waste pump 56, namely the remainder of the mixture of sample and diluent from the previous sample which has been drawn into waste pump 56 during the operative position described with reference to FIG. 9 will now be expelled by this pump 56 via tubes 56a and 56b and through check valve 46 to waste, with check valve 46 operating to prevent the return of this mixture into flexible tube 76, as previously explained.

Following delivery of the predetermined amounts of sample and diluent into the spinning cup 80, the cup 80 is rotated, first in one direction for a period of about 15 milliseconds and at a speed of about 500 rpm, followed by a quick stop (about 1 millisecond) and reversal of rotation in the other direction again at about the same speed and for about the same duration. Depending on the particular sample and diluent employed, such bidirectional rotation may be imparted to the cup 80 a number of times to achieve a thorough mixing of sample and diluent, as may well be appreciated by those skilled in the art.

Figure 11:
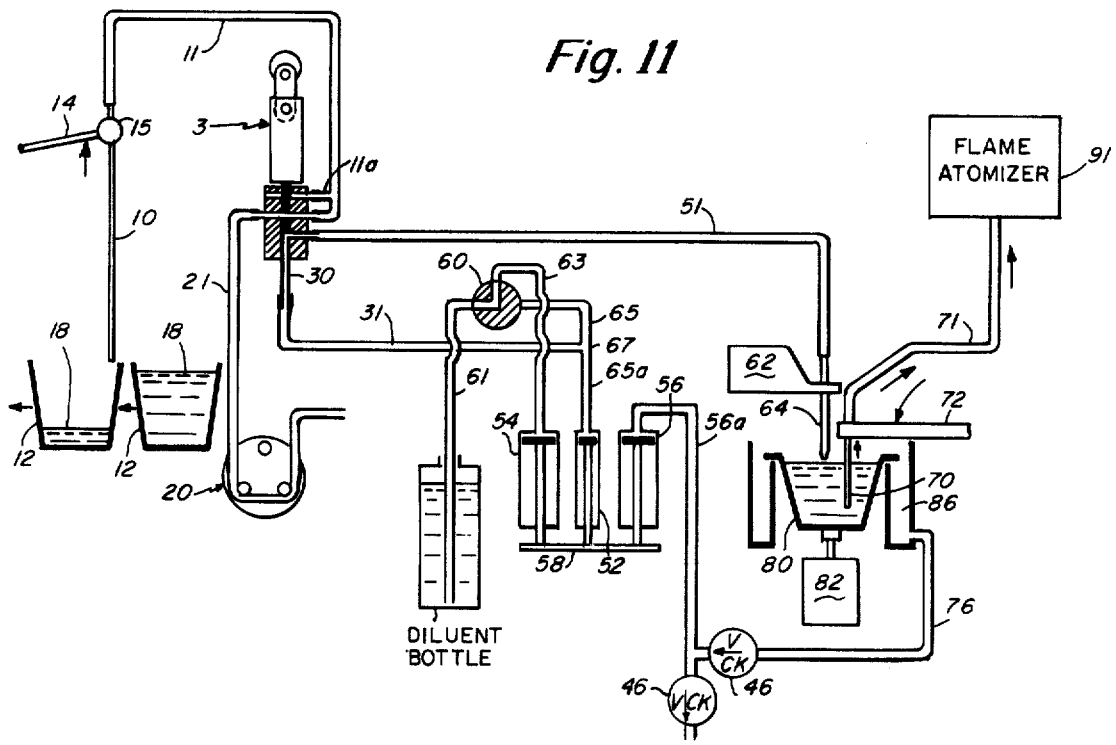

The final operative position is depicted in FIG. 11. First, it shall be noted that sample pick-up probe 10 is effectively removed from the particular sample cup 12 by the raising of its arm 14. The particular means, such as a convenient sample tray 2, containing the plurality of sample cups 12 is now indexed one station so as to present thereby another sample cup 12 containing a different fluid sample 18 to the vicinity of pick-up probe 10. The other significant step involves aspirator probe 70 which by its solenoid-operated arm 72 is for the first time lowered into its second operative position so as to enter the mixture of sample and diluent in spinning cup 80, which preferably has now been brought to a standstill. Following the entry of aspirator probe 70 into the mixture of sample and diluent, a predetermined amount thereof is now effectively aspirated via probe 70 and flexible tube 71 into the particular scientific instrument 9, here a flame photometer, with which the sampling apparatus of the invention may be employed.

Following the aspiration by probe 70 of the required amount of mixture of sample and diluent from spinning cup 80, the operative position of the sampling apparatus of the invention will once again revert to the one described with reference to FIG. 8 above. Namely, sample pick-up probe 10 will be moved down by its arm 14 so as to enter once again a fluid sample 18 in a just-indexed sample cup 12 and, through the operation of peristaltic pump assembly 20 will commence its aspiration therefrom so as to flush it out as well as tubes 11, 21 and, of course, channel 34a of the probe assembly 3. Simultaneously therewith, spinning cup 80 is brought by its motor 82 to a high speed of rotation so as to expel the remainder of the mixture of sample and diluent from the previous sample from spinning cup 80 into its surrounding annular space 86, all as shown in FIG. 8.

Although the invention has been described above in connection with a preferred embodiment thereof, it is clear that certain modifications are possible with respect to particular applications of the sampling apparatus of the invention so that the preferred embodiment thereof shown in the drawings and described above is to be understood as being only by way of example.

What is claimed is:
1. Sampling apparatus comprising
means for aspirating a sample seriatim from a plurality of samples;
means having fluid communication with said aspirating means and including a valve having two operative positions and mounted within a housing;
means having fluid communication with said valve and designed for taking in a predetermined amount of a diluent from a diluent source in a predetermined ratio one to the other;

means for delivering said sample and diluent in said ratio to a mixing means;

means for delivering a portion of said mixture from said mixing means to an instrument; and means for expelling the remainder of said mixture from said mixing means.

2. Sampling apparatus comprising means for aspirating a sample seriatim from a plurality of samples;

means having fluid communication with said aspirating means and including a valve having two operative positions and mounted within a housing;

said valve including a valve housing provided with a pair of channels and a tubular valve body mounted for translational movement within said valve housing, said valve body having a first passage that extends axially in said tubular valve body and terminates in a sideport, and a second passage spaced from said first passage, said second passage extending transversely through said tubular valve body, whereby, in one of said operative positions of said valve, its said side port is aligned with one of said pair of channels, and in the second operative position of said valve, its said side port is aligned with the other of said pair of channels;

means having fluid communication with said valve and designed for taking in a predetermined amount of said sample and a predetermined amount of a diluent from a diluent source in a predetermined ratio one to the other;

means for delivering said sample and diluent in said ratio to a mixing means; and means for delivering a portion of said mixture from said mixing means to an instrument.

3. Sampling apparatus comprising means for aspirating a sample seriatim from a plurality of samples;

means having fluid communication with said aspirating means and including a valve having two operative positions and mounted within a housing;

said valve including a valve housing provided with a pair of channels and a tubular valve body mounted for translational movement within said valve housing, said valve body having a first passage that extends axially in said tubular valve body and terminates in a sideport, and a second passage spaced from said first passage, said second passage extending transversely through said tubular valve body, means for effecting translational movement of said valve body comprising a rotatable member having an eccentrically mounted bolt and operatively connected to said valve body, whereby rotational displacement of said bolt effects the translational movement of said valve body, and whereby, in one of said operative positions of said valve, its said side port is aligned with one of said pair of channels, and in the second operative position of said valve, its said side port is aligned with the other of said pair of channels;

means having fluid communication with said valve and designed for taking in a predetermined amount of said sample and a predetermined amount of a diluent from a diluent source in a predetermined ratio one to the other;

means for delivering said sample and diluent in said ratio to a mixing means; and means for delivering a portion of said mixture from said mixing means to an instrument.

4. The sampling apparatus of claim 3 in which said valve body is further provided with a guide member to facilitate its said translational movement.

5. Sampling apparatus comprising means for aspirating a sample seriatim from a plurality of samples;

means having fluid communication with said aspirating means and including a valve having two operative positions and mounted within a housing;

means having fluid communication with said valve and designed for taking in a predetermined amount of said sample and a predetermined amount of a diluent from a diluent source in a predetermined ratio one to the other;

said means for taking in a predetermined amount of said sample and a predetermined amount of a diluent comprising two positive displacement piston-cylinder pumps driven by a common member in which said predetermined amounts of both said sample and dilunet are each determined by the respective diameters of said pumps and the degree of displacement of the pistons thereof, and said predetermined ratio of said sample to said diluent is determined by the relationship of said cylinders' diameters to one another;

means for delivering said sample and diluent in said ratio to a mixing means; and means for delivering a portion of said mixture from said mixing means to an instrument.

6. The sampling apparatus of claim 5 in which said common drive member is driven by a roller eccentrically mounted on a rotatable member, said roller designed to engage a slot formed in said common drive member.

7. The sampling apparatus of claim 1 in which said means for expelling the remainder of said mixture includes an annular space provided about said mixing means, a pump means having fluid communication with said annular space, and further including a valve for preventing the mixture withdrawn from said annular space by said pump from returning to said annular space when the same is pumped to waste.

8. Sample apparatus comprising means for aspirating a sample at a place remote from the place of delivery from a means designed to present a plurality of samples seriatim to said first means;

a valve assembly having fluid communication with said aspirating means and including a first valve member having two operative positions and mounted adjacent a second valve member provided with at least two channels, said first valve member provided with first and second ports with said first port aligning respectively with one of said channels depending on its said two operative positions;

fluid metering means having fluid communication with said valve assembly and designed for taking in a set amount of said sample and a set amount of a diluent from a source of diluent in a predetermined ratio one to the other and also including a valve means, said fluid metering means including two positive displacement piston-cylinder pumps driven by a common member in which said predetermined ratio is determined by the respective diameters of the cylinders of said pumps;

means for delivering said predetermined ratio of sample and diluent to a means for mixing the same; and means for delivering a portion of said mixture to an instrument at a place remote from said place of aspiration.

9. Sample apparatus comprising means for aspirating a sample at a place remote from the place of delivery from a means designed to present a plurality of samples seriatim to said first means;

a valve assembly having fluid communication with said aspirating means and including a first valve member having two operative positions and mounted adjacent a second valve member provided with at least two channels, said first valve member provided with first and second ports with said first port aligning respectively with one of said channels depending on its said two operative positions;

fluid metering means having fluid communication with said valve assembly and designed for taking in a set amount of said sample and a set amount of a diluent from a source of diluent in a predetermined ratio one to the other and also including a valve means, means for delivering said predetermined ratio of sample and diluent to a means for mixing the same;

means for delivering a portion of said mixture to an instrument at a place remote from said place of aspiration; and means for expelling the remainder of said mixture from said mixing means.

10. The sampling apparatus of claim 8 in which said valve assembly is provided with a means for effecting movement of said first valve member from one of its said operative positions to the other.

11. The sampling apparatus of claim 10 in which said means for effecting movement of said first valve member comprises a rotatable member having an eccentrically mounted bolt and operatively connected to said first valve member, whereby rotational displacement of such bolt effects the translational movement of said first valve member.

12. The sampling apparatus of claim 11 in which said first valve member is further provided with a guide member to facilitate its said translational movement.

13. The sampling apparatus of claim 9 in which said fluid metering means comprises positive displacement piston-cylinder pumps driven by a common member in which said set amounts are determined by the respective diameters of said pumps and the degree of displacement of the pistons of said pumps, and said predetermined ratio is determined by the relationship of said cylinders' diameters one to the other.

14. The sampling apparatus of claim 13 in which said common drive member is driven by a roller eccentrically mounted on a rotatable member, said roller designed to engage a slot formed in said common drive member.

15. The sampling apparatus of claim 9 in which said means for expelling the remainder of said mixture includes an annular space provided about said mixing means, a pump means having fluid communication with said annular space, and further including a valve for preventing the mixture withdrawn from said annular space by said pump from returning to said annular space when the same is pumped to waste.

16. Sampling apparatus comprising inlet means, delivery means remote from said inlet means, fluid metering means comprising a first volumetric metering mechanism for metering a set amount of sample fluid, and a second volumetric metering mechanism for metering a set amount of a second fluid, means defining a fluid storage region connected between said valve assembly and said first metering mechanism for storing said set amount of sample fluid, and a valve assembly having fluid communication with said inlet means, with said storage region, and with said delivery means, said valve assembly having a priming condition for flowing sample fluid through said valve assembly from said inlet means in a flushing and priming action, a metering condition for flowing a predetermined volume of sample fluid through said valve assembly into said storage region, and a delivery condition for flowing said set amount of sample fluid from said storage region through said valve assembly together with said set amount of second fluid in predetermined ratios to one another for delivery to said delivery means.

17. The sampling apparatus of claim 16 in which said valve assembly includes first and second valve members movable relative to one another, said first valve member having a first port connected to said inlet means, a second port connected to said delivery means and a third port connected to said storage region and said second valve member having a passage that connects said first and third ports in a first valve position and that connects said second and third ports in a second valve position.

18. The sampling apparatus of claim 17 and further including mixing means for receiving said sample fluid and said second fluid from said delivery means, means for delivering a portion of the mixture of said sample and second fluids from said mixing means to an instrument, and means for expelling the remainder of said mixture from said mixing means.

19. Sampling apparatus comprising a sample probe adapted to be inserted into a sample container for extracting a sample fluid from the container, a diluent reservoir, sample fluid metering means for withdrawing a set amount of sample fluid from said sample container through said sample probe, diluent metering means for withdrawing a set amount of diluent fluid from said diluent reservoir, a delivery probe for delivering a mixture of fluid sample and diluent, a valve assembly having a sample port connected to said sample probe, a delivery port connected to said delivery probe, and a meter port connected to said sample metering means by conduit structure of volume greater than said set amount of sample fluid, valve means having a first port connected to said diluent reservoir, a second port connected to said diluent metering means, and a third port connected to said conduit structure, first control means for shifting said valve assembly between a first position in which said sample port is connected to said conduit structure and a second position in which said delivery port is connected to said conduit structure and for shifting said valve means between a first position in which said first port is connected to said second port and a second position in which said second port is connected to said third port, and second control means for operating said sample and diluent metering means concurrently when said first and second valves are in their respective first positions to store said set amount of sample fluid in said conduit structure and to store said set amount of diluent fluid and for operating said sample and diluent metering means when said valve assembly and said valve means are in their respective second positions to flow said set amounts of said sample and diluent fluid through said valve assembly to said delivery probe.

20. The sampling apparatus of either claim 16 or 19 and further including a priming pump and wherein said valve assembly has a priming port connected to said priming pump.

* * * * *